United States Patent
Sawhney et al.

[11] Patent Number: 6,083,524
[45] Date of Patent: Jul. 4, 2000

[54] POLYMERIZABLE BIODEGRADABLE POLYMERS INCLUDING CARBONATE OR DIOXANONE LINKAGES

[75] Inventors: Amarpreet S. Sawhney, Bedford; David J. Enscore, Sudbury; Stephen D. Goodrich, Woburn; William C. Nason, Westford; Fei Yao, North Andover; Douglas Weaver, Bedford; Peter K. Jarrett, Sudbury; Arthur J. Coury, Boston; Ronald S. Rudowsky, Sudbury; Michelle D. Powell, Tewksbury; Luis Z. Avila, Arlington; Shikha P. Barman, Bedford, all of Mass.

[73] Assignee: Focal, Inc., Lexington, Mass.

[21] Appl. No.: 08/944,739

[22] Filed: Oct. 6, 1997

Related U.S. Application Data

[63] Continuation-in-part of application No. 08/710,689, Sep. 23, 1996, Pat. No. 5,900,245.

[51] Int. Cl.[7] ............................. A61R 2/02; A61K 31/74
[52] U.S. Cl. ........................................ 424/426; 514/772.3
[58] Field of Search ........................... 424/426; 514/772.3

[56] References Cited

U.S. PATENT DOCUMENTS

| | | |
|---|---|---|
| 2,155,658 | 1/1939 | Hermann et al. . |
| 2,210,817 | 8/1940 | Peterson . |
| 2,517,985 | 8/1950 | Bohl . |
| 2,668,162 | 2/1954 | Love . |
| 2,683,136 | 7/1954 | Higgins . |
| 2,703,316 | 3/1955 | Schneider . |
| 2,789,968 | 4/1957 | Reynolds et al. . |
| 2,917,410 | 12/1959 | Vitalis . |
| 2,962,524 | 11/1960 | Hostettler et al. . |
| 3,021,310 | 2/1962 | Cox et al. . |
| 3,030,331 | 4/1962 | Goldberg . |
| 3,046,255 | 7/1962 | Strain et al. . |

(List continued on next page.)

FOREIGN PATENT DOCUMENTS

| | | |
|---|---|---|
| 1080740 | 1/1980 | Canada . |
| 0 152 833 A2 | 8/1986 | European Pat. Off. . |
| 0 258 749 | 3/1988 | European Pat. Off. . |
| 0 370 646 A2 | 5/1990 | European Pat. Off. . |
| 0 370 646 B1 | 5/1990 | European Pat. Off. . |
| 0 587 357 A2 | 3/1994 | European Pat. Off. . |
| 0 588 853 B1 | 3/1994 | European Pat. Off. . |
| 0 610 731 A1 | 8/1994 | European Pat. Off. . |
| 0 635 276 A1 | 1/1995 | European Pat. Off. . |

(List continued on next page.)

OTHER PUBLICATIONS

ACS Meeting Briefs, "Carbonate Copolymers: New branch of epoxybutene tree," *C& EN* p. 59 (1997).

Aida, et al., "Alternating Copolymerization of Carbon Dioxide and Epoxide Catalyzed by the Aluminum Porphyrin–Quaternary Organic Salt or—Triphenylphosphine System. Synthesis of Polycarbonate with Well–Controlled Molecular Weight," *Macromolecules* 19:8–13 (1986).

(List continued on next page.)

*Primary Examiner*—Carlos A. Azpuru
*Attorney, Agent, or Firm*—Arnall Golden & Gregory, LLP

[57] ABSTRACT

Water-soluble macromers including at least one hydrolysable linkage formed from carbonate or dioxanone groups, at least one water-soluble polymeric block, and at least one polymerizable group, and methods of preparation and use thereof are described. The macromers are preferably polymerized using free radical initiators under the influence of long wavelength ultraviolet light or visible light excitation. Biodegradation occurs at the linkages within the extension oligomers and results in fragments which are non-toxic and easily removed from the body. The macromers can be used to encapsulate cells, deliver prophylactic, therapeutic or diagnostic agents in a controlled manner, plug leaks in tissue, prevent adhesion formation after surgical procedures, temporarily protect or separate tissue surfaces, and adhere or seal tissues together.

36 Claims, 2 Drawing Sheets

6,083,524
Page 2

U.S. PATENT DOCUMENTS

| | | |
|---|---|---|
| 3,063,968 | 11/1962 | Schultz . |
| 3,157,622 | 11/1964 | Goldberg . |
| 3,161,615 | 12/1964 | Goldberg . |
| 3,169,121 | 2/1965 | Goldberg . |
| 3,223,083 | 12/1965 | Cobey . |
| 3,268,486 | 8/1966 | Klootwijk . |
| 3,268,487 | 8/1966 | Klootwijk . |
| 3,297,033 | 1/1967 | Schmitt et al. . |
| 3,301,824 | 1/1967 | Hostettler et al. . |
| 3,301,825 | 1/1967 | Hostettler et al. . |
| 3,305,605 | 2/1967 | Hostettler et al. . |
| 3,312,753 | 4/1967 | Bailey, Jr. et al. . |
| 3,378,693 | 4/1968 | Hostettler et al. . |
| 3,438,374 | 4/1969 | Falb et al. . |
| 3,442,871 | 5/1969 | Schmitt et al. . |
| 3,463,158 | 8/1969 | Schmitt et al. . |
| 3,531,561 | 9/1970 | Trehu . |
| 3,552,986 | 1/1971 | Bassemir et al. . |
| 3,620,118 | 11/1971 | Kolshikawa . |
| 3,626,948 | 12/1971 | Glik et al. . |
| 3,629,374 | 12/1971 | Lundberg et al. . |
| 3,639,503 | 2/1972 | Matzner . |
| 3,641,200 | 2/1972 | Matznar . |
| 3,739,773 | 6/1973 | Schmitt et al. . |
| 3,784,585 | 1/1974 | Schmitt et al. . |
| 3,795,701 | 3/1974 | Jenkins et al. . |
| 3,839,297 | 10/1974 | Wasserman et al. . |
| 3,865,723 | 2/1975 | Marchisio et al. . |
| 3,867,190 | 2/1975 | Schmitt et al. . |
| 3,875,937 | 4/1975 | Schmitt et al. . |
| 3,882,192 | 5/1975 | Elghani et al. . |
| 3,896,802 | 7/1975 | Williams . |
| 3,937,223 | 2/1976 | Roth . |
| 3,939,049 | 2/1976 | Ratner et al. . |
| 3,960,152 | 6/1976 | Augurt et al. . |
| 3,966,788 | 6/1976 | Senet et al. . |
| 3,981,766 | 9/1976 | Schmitt et al. . |
| 3,982,543 | 9/1976 | Schmitt et al. . |
| 4,033,936 | 7/1977 | Augurt et al. . |
| 4,045,418 | 8/1977 | Sinclair . |
| 4,057,537 | 11/1977 | Sinclair . |
| 4,066,630 | 1/1978 | Dixon et al. . |
| 4,067,876 | 1/1978 | Ferruti et al. . |
| 4,072,704 | 2/1978 | Langdon . |
| 4,093,677 | 6/1978 | Ferruti et al. . |
| 4,104,264 | 8/1978 | Dixon et al. . |
| 4,137,280 | 1/1979 | Dixon et al. . |
| 4,137,921 | 2/1979 | Okuzumi et al. . |
| 4,143,017 | 3/1979 | Tarumi et al. . |
| 4,145,525 | 3/1979 | Dixon et al. . |
| 4,146,320 | 3/1979 | Ferruti et al. . |
| 4,157,437 | 6/1979 | Okuzumi et al. . |
| 4,166,902 | 9/1979 | Ferruti et al. . |
| 4,169,923 | 10/1979 | Ferruti et al. . |
| 4,179,304 | 12/1979 | Rossomando . |
| 4,189,609 | 2/1980 | Langdon . |
| 4,211,865 | 7/1980 | Ferruti et al. . |
| 4,223,011 | 9/1980 | Ferruti et al. . |
| 4,239,861 | 12/1980 | Braese et al. . |
| 4,243,775 | 1/1981 | Rosensaft et al. . |
| 4,264,425 | 4/1981 | Dal Pozzo et al. . |
| 4,264,752 | 4/1981 | Watson, Jr. . |
| 4,297,455 | 10/1981 | Lindner et al. . |
| 4,300,565 | 11/1981 | Rosensaft et al. . |
| 4,303,066 | 12/1981 | D'Andrea . |
| 4,316,001 | 2/1982 | Boileau et al. . |
| 4,330,481 | 5/1982 | Timberlake et al. . |
| 4,354,487 | 10/1982 | Oczkowski et al. . |
| 4,415,502 | 11/1983 | Timberlake et al. . |
| 4,429,080 | 1/1984 | Casey et al . |
| 4,436,839 | 3/1984 | Behnke et al. . |
| 4,452,973 | 6/1984 | Casey et al. . |
| 4,503,216 | 3/1985 | Fagerburg et al. . |
| 4,511,478 | 4/1985 | Nowinski et al. . |
| 4,526,938 | 7/1985 | Churchill et al. . |
| 4,559,945 | 12/1985 | Koelmel et al. . |
| 4,632,929 | 12/1986 | Mattei et al. . |
| 4,643,191 | 2/1987 | Bezwada et al. . |
| 4,653,497 | 3/1987 | Bezwada et al. . |
| 4,699,974 | 10/1987 | Evans . |
| 4,705,820 | 11/1987 | Wang et al. . |
| 4,716,203 | 12/1987 | Casey et al. . |
| 4,727,134 | 2/1988 | Brunelle et al. . |
| 4,741,872 | 5/1988 | De Luca et al. . |
| 4,745,160 | 5/1988 | Churchill et al. . |
| 4,760,117 | 7/1988 | Evans et al. . |
| 4,768,523 | 9/1988 | Cahalan et al. . |
| 4,769,388 | 9/1988 | Ferruti et al. . |
| 4,781,183 | 11/1988 | Casey et al. . |
| 4,788,879 | 12/1988 | Jarrett et al. . |
| 4,791,929 | 12/1988 | Jarrett et al. . |
| 4,804,691 | 2/1989 | English et al. . |
| 4,826,945 | 5/1989 | Cohn et al. . |
| 4,846,165 | 7/1989 | Hare et al. . |
| 4,867,602 | 9/1989 | Casey et al. . |
| 4,882,168 | 11/1989 | Casey et al. . |
| 4,891,263 | 1/1990 | Kotliar et al. . |
| 4,900,797 | 2/1990 | Leitz et al. . |
| 4,916,193 | 4/1990 | Tang et al. . |
| 4,920,203 | 4/1990 | Tang et al. . |
| 4,929,750 | 5/1990 | Ferruti et al. . |
| 4,938,763 | 7/1990 | Dunn et al. . |
| 4,942,035 | 7/1990 | Churchill et al. . |
| 4,944,767 | 7/1990 | Barbucci et al. . |
| 4,960,866 | 10/1990 | Bendix et al. . |
| 4,961,890 | 10/1990 | Boyer . |
| 4,965,300 | 10/1990 | Eichensuer et al. . |
| 4,997,722 | 3/1991 | Adler . |
| 5,009,224 | 4/1991 | Cole . |
| 5,019,094 | 5/1991 | Bezwada et al. . |
| 5,019,100 | 5/1991 | Hennink et al. . |
| 5,043,398 | 8/1991 | Auerbach et al. . |
| 5,051,272 | 9/1991 | Hermes et al. . |
| 5,061,281 | 10/1991 | Mares et al. . |
| 5,066,772 | 11/1991 | Tang et al. . |
| 5,067,961 | 11/1991 | Kelman et al. . |
| 5,076,807 | 12/1991 | Bezwada et al. . |
| 5,081,224 | 1/1992 | Ando et al. . |
| 5,100,992 | 3/1992 | Cohn et al. . |
| 5,104,957 | 4/1992 | Kelman et al. . |
| 5,116,929 | 5/1992 | Greco et al. . |
| 5,120,802 | 6/1992 | Mares et al. . |
| 5,137,800 | 8/1992 | Neckers et al. . |
| 5,146,945 | 9/1992 | Tang et al. . |
| 5,147,698 | 9/1992 | Cole . |
| 5,152,781 | 10/1992 | Tang et al. . |
| 5,156,613 | 10/1992 | Sawyer . |
| 5,160,745 | 11/1992 | De Luca et al. . |
| 5,173,301 | 12/1992 | Itoh et al. . |
| 5,177,120 | 1/1993 | Hare et al. . |
| 5,201,764 | 4/1993 | Kelman et al. . |
| 5,209,776 | 5/1993 | Bass et al. . |
| 5,225,129 | 7/1993 | van den Berg . |
| 5,226,877 | 7/1993 | Epstein . |
| 5,252,701 | 10/1993 | Jarrett et al. . |
| 5,256,764 | 10/1993 | Tang et al. . |
| 5,264,425 | 11/1993 | Dal Pozzo et al. . |
| 5,274,074 | 12/1993 | Tang et al. . |
| 5,278,200 | 1/1994 | Coury et al. . |
| 5,296,627 | 3/1994 | Tang et al. . |
| 5,308,887 | 5/1994 | Ko et al. . |
| 5,310,599 | 5/1994 | Ford . |

| | | |
|---|---|---|
| 5,324,307 | 6/1994 | Jarrett et al. . |
| 5,332,475 | 7/1994 | Mechanic . |
| 5,332,802 | 7/1994 | Kelman et al. . |
| 5,354,336 | 10/1994 | Kelman et al. . |
| 5,359,026 | 10/1994 | Gruber . |
| 5,360,892 | 11/1994 | Bonsignore et al. . |
| 5,364,700 | 11/1994 | Domeier . |
| 5,366,756 | 11/1994 | Chesterfield et al. . |
| 5,372,585 | 12/1994 | Tiefenbrun et al. . |
| 5,378,801 | 1/1995 | Reichert et al. . |
| 5,385,606 | 1/1995 | Kowanko . |
| 5,391,707 | 2/1995 | Jiang . |
| 5,397,816 | 3/1995 | Reilly et al. . |
| 5,403,347 | 4/1995 | Roby et al. . |
| 5,403,826 | 4/1995 | Kim et al. . |
| 5,410,016 | 4/1995 | Hubbell et al. . |
| 5,412,067 | 5/1995 | Shinoda et al. . |
| 5,412,068 | 5/1995 | Tang et al. . |
| 5,425,984 | 6/1995 | Kennedy et al. . |
| 5,447,966 | 9/1995 | Hermes et al. . |
| 5,449,743 | 9/1995 | Kobayashi et al. . |
| 5,459,177 | 10/1995 | Miyakoshi et al. . |
| 5,463,012 | 10/1995 | Ferruti et al. . |
| 5,468,253 | 11/1995 | Bezwada et al. . |
| 5,476,516 | 12/1995 | Kelman et al. . |
| 5,478,921 | 12/1995 | Roby et al. . |
| 5,480,427 | 1/1996 | Kelman et al. . |
| 5,484,913 | 1/1996 | Stilwell et al. . |
| 5,486,593 | 1/1996 | Tang et al. . |
| 5,496,872 | 3/1996 | Constancis et al. . |
| 5,502,158 | 3/1996 | Sinclair et al. . |
| 5,508,317 | 4/1996 | Müller . |
| 5,512,091 | 4/1996 | Steiner . |
| 5,516,825 | 5/1996 | Montador et al. . |
| 5,521,280 | 5/1996 | Reilly et al. . |
| 5,522,841 | 6/1996 | Roby et al. . |
| 5,525,646 | 6/1996 | Lundgren et al. . |
| 5,525,647 | 6/1996 | Eichmiller . |
| 5,527,864 | 6/1996 | Suggs et al. . |
| 5,529,914 | 6/1996 | Hubbell et al. . |
| 5,530,038 | 6/1996 | Yamamoto et al. . |
| 5,531,707 | 7/1996 | Kers et al. . |
| 5,531,709 | 7/1996 | Eykmann et al. . |
| 5,540,677 | 7/1996 | Sinofsky . |
| 5,550,209 | 8/1996 | Inoue et al. . |
| 5,552,452 | 9/1996 | Khadem et al. . |
| 5,554,665 | 9/1996 | Tateosign et al. . |
| 5,561,157 | 10/1996 | Yu et al. . |
| 5,563,238 | 10/1996 | Bonsignore et al. . |
| 5,567,435 | 10/1996 | Hubbell et al. . |
| 5,573,934 | 11/1996 | Hubbell et al. . |
| 5,589,563 | 12/1996 | Ward et al. . |
| 5,594,095 | 1/1997 | Gruber et al. . |
| 5,607,686 | 3/1997 | Totakura et al. . |
| 5,621,050 | 4/1997 | Jarret et al. . |
| 5,621,119 | 4/1997 | Podszun et al. . |
| 5,629,384 | 5/1997 | Veronese et al. . |
| 5,631,322 | 5/1997 | Veronese et al. . |
| 5,631,336 | 5/1997 | Ferruti et al. . |
| 5,633,342 | 5/1997 | Verser et al. . |
| 5,650,234 | 7/1997 | Dolence et al. . |
| 5,658,995 | 8/1997 | Kohn et al. . |
| 5,665,428 | 9/1997 | Cha et al. . |
| 5,665,474 | 9/1997 | Gruber et al. . |
| 5,698,213 | 12/1997 | Jamiolkowski et al. . |
| 5,698,661 | 12/1997 | Ferruti et al. . |

FOREIGN PATENT DOCUMENTS

| | | |
|---|---|---|
| 0 390 860 B1 | 4/1995 | European Pat. Off. . |
| 0 737 703 A2 | 4/1995 | European Pat. Off. . |
| 2 206 144 | 2/1972 | Germany . |
| 28 60 824 A1 | 5/1980 | Germany . |
| 44 02 590 A1 | 8/1994 | Germany . |
| 622 677 62 | 5/1986 | Japan . |
| 5310808 | 5/1992 | Japan . |
| 965085 | 7/1960 | United Kingdom . |
| 1332505 | 10/1973 | United Kingdom . |
| 1414600 | 2/1974 | United Kingdom . |
| 92/15340 | 9/1992 | WIPO . |
| 92/22600 | 12/1992 | WIPO . |
| 93/16687 | 9/1993 | WIPO . |
| 93/17669 | 9/1993 | WIPO . |
| 95/12629 | 5/1995 | WIPO . |
| 96/11671 | 4/1996 | WIPO . |
| 96/29370 | 9/1996 | WIPO . |
| 97/25067 | 7/1997 | WIPO . |
| 97/25366 | 7/1997 | WIPO . |
| 97/29145 | 8/1997 | WIPO . |

OTHER PUBLICATIONS

Bailey, et al., "Synthesis of Poly–ϵ–Caproictone via a Free Radical Mechanism, Free Radical Ring–Opening Polymerization of 2–Methylene–1,3–Dioxepane," *Journal of Polymer Science* 20:3021–3030 (1982).

Barrows, "Degradable implant materials: A review of synthetic absorbable polymers and their applicatios," *Clinical Materials* 1:233–257 (1986).

Chen, et al., "Novel Graft Copolymers of a Temperature–Sensitive Polymer Grafted to a pH–Sensitive, Bioadhesive Polymer for Controlled Drug Delivery," *21st Annual Meeting of the Society of Biomaterials* (1995).

CIMA, et al., "Hepatocyte Responses to PEO–Tethered Carbohydrates Depend on Tether Conformation," *21st Annual Meeting of the Society of Biomaterials* 147 (1995).

Constancis, et al., "Colcys as Surgical Adhesives, Ex Vivo Characterization of Mechanical and Adhesive Properties," *21st Annual Meeting of the Society of Biomaterials* 258 (1995).

Dumanian, et al., "A New Photopolymerizable Blood Vessel Glue that Seals Human Vessel Anastomoses Without Augmenting Thrombogenicity," *Plastic and Reconstructive Surgery* 95(5):901–907 (1995).

Dupont, et al., "Collagen Gel Sealant (Glue) Based On Controlled Oxidized Collagen Ex Vivo and In Vivo Characterization," *21st Annual Meeting of the Society of Biomaterials* 242 (1995).

Frenkel, et al., "A Collagen Bilayer Implant for Articular Cartilage Repair in a Rabbit Model," *21st Annual Meeting of the Society of Biomaterials* 305 (1995).

Gagnieu, et al., "Colcys: New Crosslinkable Atelocollagens Synthesis and physico–chemical properties of highly grafted polymers," *21st Annual Meeting of the Society of Biomaterials* 256 (1995).

Gershkovich, et al., "Post–Surgical Adhesion Prevention with Bioresorbable Gels of Amine Modified Hyaluronic Acid," *21st Meeting of the Society of Biomaterials* 66 (1995).

Hata, et al., "Enzymatic Polymerization of 2–Hydroxyethylmethacrylate for Artificial Embolization," *The Third Word Biomaterials Congress* 301 (1988).

Herbert, et al., "Polytetramethylene Oxide Blended With Polyurethane Reduces Platelet Adhesion", *21st Annual Meeting of the Society of Biomaterials* 271 (1995).

Hsu, et al., "Study On Aqueous Polymerizations Of Vinyl Monomers Initiated By Metal Oxidant–Chelating Agent Redox Initiators", *J. Polymer Science: Part A: Polymer Chem.* 31:3213–3222 (1993).

Inoue, "Copolymerization of Carbon Dioxide," *Department of Synthetic Chemistry, Faculty of Engineering,* University of Tokyo, 1–42 (1974).

Inoue, et al., "Synthesis and Thermal Degradation of Carbon Dioxide–Epoxide Copolymer," *Applied Polymer Symposium* 26:257–267 (1975).

Inoue, "Copolymerization of Carbon Dioxide and Epoxide: Functionality of the Copolymer," *J. Macromol. Sci. Chem.* A13(5):651–664 (1979).

Kawaguchi, et al., "Release Profiles of 5–Fluorouracil and Its Derivative from Polycarbonate Matrices in Vitro," *Chem. Pharm. Bull.* 30(4):1517–1520 (1982).

Kawaguchi, et al., "Examination of Biodegradability of Poly(ethylene carbonate) and Poly(propylene carbonate) in the Peritoneal Cavity in Rats," *Chem. Pharm. Bull.* 31(4:1400–1403 (1983).

Keul, et al., "Anionic ring–opening polymerization of 2,2–dimethyltrimethylene carbonate," *Makromol. Chem.* 187:2579–2589 (1986).

Kobayashi, et al., "Water–curable and Biodegradable prepolymers," *Journal of Biomedical Materials Research* 25:1481–1494 (1991).

Kojima, et al., "Preparation and Evaluation in Vitro of Polycarbonate Microspheres Containing Local Anesthetics," *Chem. Pharm. Bull.* 32(7):2795–2802 (1984).

Kricheldorf, et al., "Polylactones. 16. Cationic Polymerization of Trimethylene Carbonate and Other Cyclic Carbonates," *J. Macromol. Sci.—Chem.* A26(4):631–644 (1989).

Kricheldorf, et al., "Polymers of Carbonic Acid, 12—Spontaneous and Hematin–Initiated Polymerizations of Trimethylene Carbonate and Neopentylene Carbonate," *Macromol. Chem. Phys.* 197:1043–1054 (1996).

McPherson, et al., "Scaling Analysis of the Prevention of Protein Adsorption by Grafted PEO Chains," *21st Annual Meeting of the Society of Biomaterials* 224 (1995).

Miller, et al., "Prevention of Post–Surgical Tendon Adhesions Using Hyaluronic Acid Systems," *21st Annual Meeting of Society of Biomaterials* 382 (1995).

Moore, et al., An Injectable Biodegradable Drug Delivery System Based on Acrylic Terminated Poly($\epsilon$–Caprolactone), *21st Annual Meeting of the Society of Biomaterials* 186 (1995).

Mouritzen, et al., "The effect of fibrin glueing to seal bronchial and alveolar leakages after pulmonary resections decortications," *Eur. J. Cardio–thorac Surg.* 7(2):75–80 (1993).

Müller, et al., "Lithium and Potassium Alcoholates of Poly-(ethylene–glycol)s as Initiators for the Anionic Polymerization of 2,2–Dimethyltrimethylene Carbonate. Synthesis of AB and ABA Block Copolymers," *Euro. Polym. J.* 27(12):1323–1330 (1991).

Pemberton, et al., "Polymerization of vinyl acetate using visible radiation and a dye–reducing agent sensitizer: 1. Pre–initiation and initiation reactions involving ethyl eosin and ascorbic acid," *Polymer* 25:536–542 (1984).

Pemberton, et al., "Polymerization of vinyl acetate using visible radiation and a dye–reducing agent sensitizer: 2. Kinetic studies and polymerization mechanism," *Polymer* 25:543–549 (1984).

Reed, "In Vivo and In Vitro Studies of Biodegradable Polymers for Use in Medicine," Thesis submitted in accordance with the requirements of the University of Liverpool for the degree of Doctor of Philosophy (Jul., 1978).

Rimpler, "Gluing—a challenge in surgery," *Int. J. Adhesion and Adhesives* 16:17–20 (1996).

Roby, et al., "Absorbable Sutures Based on Glycolide/ Trimethylene Carbonate Copolymers," *21st Annual Meeting of the Society of Biomaterials* 216 (1985).

Sawhney, et al., "Optimization of photopolymerized bioerodible hydrogel properties for adhesion prevention," *Journal of Biomedical Materials Research* 28(7):831–838 (1994).

Sierra, et al., "Skullbase Cerebrospinal Fluid Leakage Control With a Fibrin–based Composite Tissue Adhesive," *21st Annual Meeting of the Society of Biomaterials* 247 (1995).

Takanashi, et al., "Functional Polycarbonate by Copolymerization of Carbon Dioxide and Epoxide: Synthesis and Hydrolysis," *Makromol. Chem.* 183:2085–2092 (1982).

Tardy, et al., "New Surgical Sealant (Glue) Based on Controlled Oxidized Collage—Design and Physico–Chemical Characterization," *21st Annual Meeting of the Society of Biomaterials* 254 (1995).

Tiollier, et al., "Novel Development of Collagen/Gelatin Surgical Adhesives for Surgical Soft Tissue Applications," *21st Annual Meeting of the Society of Biomaterials* 257 (1995).

Tiollier, et al., "Colcys as Surgical Adhesives—In Vivo Characterization and Biocompatability," *21st Annual Meeting of the Society of Biomaterials* (1995).

Tomizawa, et al., "Polyepoxy Compound Cross–Linked Cotton Type Collagen Hemostat," *21st Annual Meeting of the Society of Biomatrials* 273 (1995).

Truong, et al., "In Vitro Conditions for Accelerated Hydrolysis of Bioabsorbable Fibers," *21st Annual Meeting of the Society of Biomaterials* 436 (1995).

POLYMERIZABLE BIODEGRADABLE POLYMERS INCLUDING CARBONATE OR DIOXANONE LINKAGES

This application is a continuation-in-part of U.S. Ser. No. 08/710,689 entitled "*Compliant Tissue Sealants*" filed Sep. 23, 1996, by Amarpreet S. Sawhney, Michelle D. Lyman, Peter K. Jarrett, and Ronald S. Rudowsky, now U.S. Pat. No. 5,900,245.

FIELD OF THE INVENTION

The present invention relates to improved photopolymerizable biodegradable hydrogels for use as tissue adhesives, coatings, sealants and in controlled drug delivery devices. The improved materials incorporate carbonate and/or dioxanone linkages. These biodegradable linkages allow improved control of various properties of the macromers, particularly increasing viscosity while preserving biodegradability.

BACKGROUND OF THE INVENTION

U.S. Pat. No. 5,410,016 to Hubbell et al. discloses biocompatible, biodegradable macromers which can be polymerized to form hydrogels. The macromers are block copolymers that include a biodegradable block, a water-soluble block with sufficient hydrophilic character to make the macromer water-soluble, and one or more polymerizable groups. The polymerizable groups are separated from each other by at least one degradable group. Hubbell specifically discloses using polyhydroxy acids, such as polylactide, polyglycolide and polycaprolactone as the biodegradable polymeric blocks. One of the disclosed uses for the macromers is to plug or seal leaks in tissue.

Other hydrogels have been described, for example, in U.S. Pat. No. 4,938,763 to Dunn et al., U.S. Pat. Nos. 5,100,992 and 4,826,945 to Cohn et al., U.S. Pat. Nos. 4,741,872 and 5,160,745 to De Luca et al., U.S. Pat. No. 5,527,864 to Suggs et al., and U.S. Pat. No. 4,511,478 to Nowinski et al. Methods of using such polymers are described in U.S. Pat. No. 5,573,934 to Hubbell et al. and PCT WO 96/29370 by Focal.

While numerous references disclose using homopolymers and copolymers including carbonate linkages to form solid medical devices, such as sutures, suture coatings and drug delivery devices (see, for example, U.S. Pat. No. 3,301,824 to Hostettler et al., U.S. Pat. No. 4,243,775 to Rosensaft et al., U.S. Pat. No. 4,429,080 to Casey et al., U.S. Pat. No. 4,716,20 to Casey et al., U.S. Pat. No. 4,857,602 to Casey et al., U.S. Pat. No. 4,882,168 to Casey, EP 0 390 860 B1 by Boyle et al., U.S. Pat. No. 5,066,772 to Tang et al., U.S. Pat. No. 5,366,756 to Chesterfield et al., U.S. Pat. No. 5,403,347 to Roby et al. and U.S. Pat. No. 5,522,841 to Roby et al.), none of these publications discloses incorporating polymerizable groups on the polymers so that the polymers can be further polymerized. Accordingly, none of these polymers can be used in the same manner as the macromers in U.S. Pat. No. 5,410,016 to Hubbell et al.

Sealing or plugging holes in lung tissue is inherently more difficult than sealing other types of tissue because the tissue is constantly expanded and contracted during normal respiration. It would be advantageous to provide macromers which can be rapidly polymerized in vivo to form hydrogels which are more elastic than conventional hydrogels, for example, for use in sealing lung tissue.

It is therefore an object of the present invention to provide biodegradable, biocompatible macromers that can be rapidly polymerized in vivo to form hydrogels which are more elastic than conventional hydrogels.

It is a further object of the present invention to provide a macromer solution which can be administered during surgery or outpatient procedures and polymerized as a tissue adhesive, cell encapsulating medium, tissue sealant, wound dressing or drug delivery device.

It is a still further object of the present invention to provide a macromer solution which can be polymerized in vivo on a surface to be coated in a very short time frame to form conformal coating layers.

SUMMARY OF THE INVENTION

Biocompatible, biodegradable, polymerizable and at least substantially water-soluble macromers and methods of preparation and use thereof are disclosed. The macromers are block copolymers that include at least one water-soluble block, at least one biodegradable block, and at least one polymerizable group. At least one of the biodegradable blocks comprises a linkage based on a carbonate or dioxanone group, and the macromers can contain other degradable linkages or groups in addition to carbonate or dioxanone.

The carbonate and dioxanone linkages impart more elasticity to the polymer and degrade at a different rate than hydroxy acid linkages. Carbonate linkages can also increase macromer viscosity, at a given concentration, without requiring increased molecular weight of the nondegradable components of the macromer. The macromers can also include poly(hydroxy acid) linkages which degrade by hydrolysis into relatively non-toxic hydroxy acid residues, or other biodegradable blocks such as polycaprolactones, polyorthoesters, polyanhydrides, and polypeptides. The degradation time of the polymers can be controlled, for example, by selecting the types and proportion of the biodegradable blocks.

The polymerizable groups can be polymerized by either free radical (homolytic) processes or by heterolytic processes (such as cationic polymerization). Preferably, the groups are polymerized photochemically. The macromer can be polymerized in the presence of prophylactic, therapeutic or diagnostic agents, for delivery of the incorporated agents in a controlled manner as the resulting polymer degrades. The macromers are useful for delivering hydrophobic, hydrophilic and/or labile materials. They can be particularly useful for delivery of hydrophobic materials.

The macromers can be polymerized in an interfacial manner to form ultrathin coatings which are intimately adhered to the coated surface, or in a bulk manner to form relatively thick coatings which may or may not be intimately adhered to the coated surface. Alternatively, the two methods can be combined to provide a relatively thick coating which is intimately adhered to the surface. Each of these methods is advantageous for certain applications.

DETAILED DESCRIPTION OF THE INVENTION

Polymers

Figure 1:
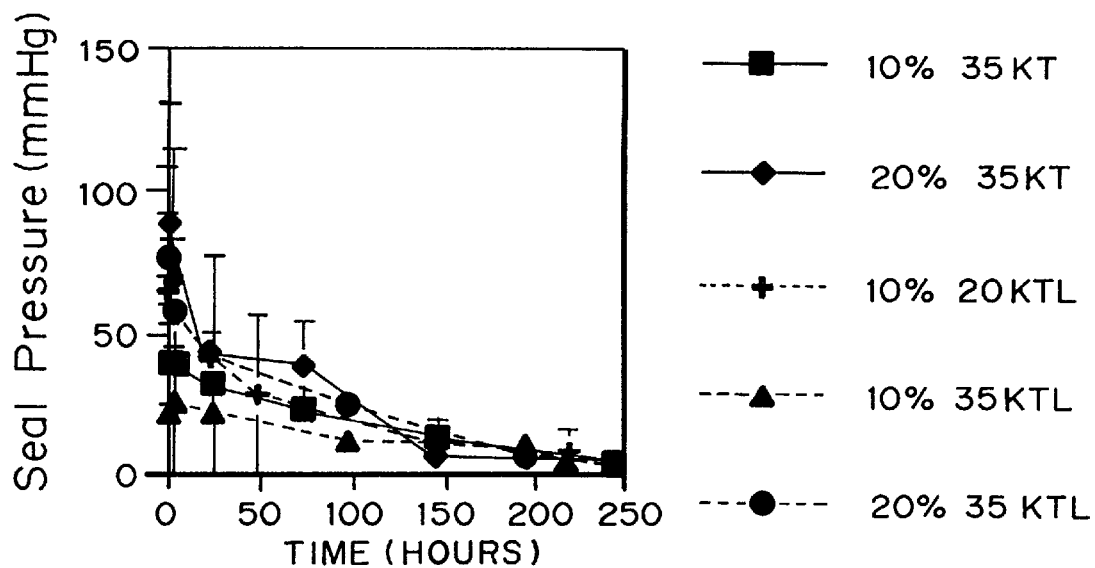
FIG. 1 is a graph of the elastic strength (seal pressure, mm Hg) over time (hr) of five different sealant materials: 10% 35K T, 20% 35K T, 10% 20K TL, 10% 20 K TL, and 20% 35K TL K is defined as 100 Daltons (weight average molecular weight, T is trimethylene carbonate (TMC), L is lactide, and TL is a copolymer of TMC and lactide.

Water-soluble, biocompatible, biodegradable macromers and methods of preparation and use thereof, are disclosed. The macromers include at least one water-soluble block, at least one biodegradable block, and at least one polymerizable group. At least one biodegradable block contains a carbonate or dioxanone group. To obtain a biodegradable material after polymerization, each polymerizable group must be separated from any other polymerizable group on the macromer by at least one biodegradable linkage or group.

At least a portion of the macromers will contain more than one reactive group and thereby be effective as crosslinkers, so that the macromers can be crosslinked to form a gel. The minimal proportion required will vary with the nature of the macromer and its concentration in solution, and the proportion of crosslinker in the macromer solution can be as high as 100% of the macromer solution.

For example, the macromers include at least 1.02 polymerizable groups on average, and, more preferably, the macromers each include two or more polymerizable groups on average.

Since in the preferred homolytic (free radical) polymerization reactions each polymerizable group will polymerize into a chain, crosslinked hydrogels can be produced using only slightly more than one reactive group per macromer (i.e., about 1.02 polymerizable groups on average). However, higher percentages are preferable, and excellent gels can be obtained in polymer mixtures in which most or all of the molecules have two or more reactive double bonds. Poloxanines, an example of a water-soluble block, have four arms and thus may readily be modified to include four polymerizable groups.

As used herein, a "biocompatible" material is one which stimulates only a mild, often transient, implantation response, as opposed to a severe or escalating response.

As used herein, a "biodegradable" material is one which decomposes under normal in vivo physiological conditions into components which can be metabolized or excreted.

As used herein, a "block" is a region of a copolymer differing in subunit composition from neighboring regions. Blocks will generally contain multiple subunits, up to about one thousand subunits or less for non-degradable materials, and without an upper limit for degradable materials. In the lower limit, the size of a block depends on its function; the minimum size is that which is sufficient to allow the function to be performed. In the case of a block conferring water-solubility on the macromer, this will be typically 400 daltons or more, preferably 600 daltons or more, more preferably at least 1000 daltons, and most preferably in the range of 2000 to 40,000 daltons. For degradable linkages, the minimum block size is a single linkage of the appropriate degradability for the function. More preferably, the block size is two to forty groups; most preferably, three to twenty. The reactive groups may be considered as a block for some purposes; the typical number of units in such a block is one, but may be two to five.

As used herein, a carbonate is a functional group with the structure —O—C(O)—O—. The carbonate starting material can be cyclic, such as trimethylene carbonate (TMC), or can be linear, such as dimethylcarbonate ($CH_3O$—C(O)—$OCH_3$). After incorporation into the polymerizable macromer, the carbonate will be present at least in part as R—O—C(=O)—O—R', where R and R' are other components of the macromer.

As used herein, a dioxanone is a repeating unit with the structure —O—C(O)—R—O—, where R is a straight, branched or cyclic alkyl group. An example of a cyclic dioxanone is 1,4-dioxan-2-one. 1,4-dioxan-2-one is a preferred dioxanone.

As used herein, a hydrogel is a substance formed when an organic polymer (natural or synthetic) is cross-linked via covalent, ionic, or hydrogen bonds to create a three-dimensional open-lattice structure which entraps water molecules to form a gel.

As used herein, "water-soluble" is defined as a solubility of at least one gram/liter in an aqueous solution at a temperature in the range of about 0° C. and 50° C. Aqueous solutions can include small amounts of water-soluble organic solvents, such as dimethylsulfoxide, dimethylformamide, alcohols, acetone, and/or glymes.

Types of Block Copolymers

In general terms, the macromers are block co-polymers that comprise a biodegradable block, a water-soluble block, and at least one polymerizable group. Preferably, the macromers comprise at least 1.02 polymerizable groups on average, and, more preferably, include at least two polymerizable groups per macromer, on average. Average numbers of polymerizable groups can be obtained, for example, by blending macromers with different amounts of polymerizable groups.

The individual polymeric blocks can be arranged to form different types of block copolymers, including di-block, tri-block, and multi-block copolymers. The polymerizable blocks can be attached directly to biodegradable blocks or indirectly via water-soluble nondegradable blocks, and are preferably attached so that the polymerizable groups are separated from each other by a biodegradable block. For example, if the macromer contains a water-soluble block coupled to a biodegradable block, one polymerizable group may be attached to the water-soluble block and another attached to the biodegradable block. Preferably, both polymerizable groups would be linked to the water-soluble block by at least one degradable linkage.

The di-block copolymers include a water-soluble block linked to a biodegradable block, with one or both ends capped with a polymerizable group. The tri-block copolymers can include a central water-soluble block and outside biodegradable blocks, with one or both ends capped with a polymerizable group. Alternatively, the central block can be a biodegradable block, and the outer blocks can be water-soluble. The multiblock copolymers can include one or more of the water-soluble blocks and biocompatible blocks coupled together in a linear fashion. Alternatively, the multi-block copolymers can be brush, comb, dendritic or star copolymers. If the backbone is formed of a water-soluble block, at least one of the branches or grafts attached to the backbone is a biodegradable block. Alternatively, if the backbone is formed of a biodegradable block, at least one of the branches or grafts attached to the backbone is a water-soluble block, unless the biodegradable block is also water-soluble. In another embodiment, a multifunctional compound, such as a polyol, can be coupled to multiple polymeric blocks, at least one of which is water-soluble and at least one of which is biodegradable.

In general, any formulation of the macromer which is intended to be biodegradable must be constructed so that each polymerizable group is separated from each other polymerizable group by one or more linkages which are biodegradable. Non-biodegradable materials are not subject to this constraint.

Those skilled in the art will recognize that the individual polymeric blocks may have uniform compositions, or may have a range of molecular weights, and may be combinations of relatively short chains or individual species which confer specifically desired properties on the final hydrogel, while retaining the required characteristics of the macromer. The lengths of oligomers referred to herein may vary from single units (in the biodegradable portions) to many, subject to the constraint of preserving the overall water-solubility of the macromer.

In the discussion below and the examples, macromers are often designated by a code of the form xxKZn. xxK represents the molecular weight of the backbone polymer, which is polyethylene glycol ("PEG") unless otherwise stated, in thousands of Daltons. Z designates the biodegradable linkage, using a code wherein where L is for lactic acid, G is for glycolic acid, D is for dioxanone, C is for caprolactone, T is for trimethylene carbonate, and n is the average number of degradable groups in the block. The molecules are terminated with acrylic ester groups, unless otherwise stated. This is sometimes also indicated by the suffix A2.

While the preferred biodegradable groups (in addition to carbonate or dioxanone) are hydroxy acids, orthoesters, anhydrides, or other synthetic or semisynthetic degradable linkages, natural materials may be used in the biodegradable sections when their degree of degradability is sufficient for the intended use of the macromer. Such biodegradable groups may comprise natural or unnatural amino acids, carbohydrate residues, and other natural linkages. Biodegradation time will be controlled by the local availability of enzymes hydrolyzing such linkages. The availability of such enzymes may be ascertained from the art or by routine experimentation.

Water Soluble Regions

Suitable water-soluble polymeric blocks include those prepared from poly(ethylene glycol), poly(ethylene oxide), partially or fully hydrolyzed poly(vinyl alcohol), poly (vinylpyrrolidone), poly(ethyloxazoline), poly(ethylene oxide)-co-poly(propylene oxide) block copolymers (poloxamers and meroxapols), poloxamines, carboxymethyl cellulose, hydroxyalkylated celluloses such as hydroxyethyl cellulose and methylhydroxypropyl cellulose, polypeptides, polynucleotides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin. Preferably, the water-soluble polymeric blocks are made from poly (ethylene glycol) or poly(ethylene oxide).

The soluble polymer blocks may be intrinsically biodegradable or may be poorly biodegradable or effectively non-biodegradable in the body. In the latter two cases, the soluble blocks should be of sufficiently low molecular weight to allow excretion. The maximum molecular weight to allow excretion in human beings (or other species in which use is intended) will vary with polymer type, but will often be about 40,000 daltons or below. Water-soluble natural polymers and synthetic equivalents or derivatives, including polypeptides, polynucleotides, and degradable polysaccharides, can be used.

The water-soluble blocks can be a single block with a molecular weight of at least 600, preferably 2000 or more, and more preferably at least 3000 Daltons. Alternatively, the water-soluble blocks can be two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with degradable groups as described below, and such linking groups can be conjugated at one or both ends with hydrophilic groups such as polyethylene glycols. In another embodiment, two or more PEG molecules can be joined by biodegradable linkages including carbonate linkages, and subsequently be end-capped with polymerizable groups.

Biodegradable Blocks

The biodegradable blocks are preferably hydrolyzable under in vivo conditions. At least one biodegradable region is a carbonate or dioxanone linkage. Additional biodegradable polymeric blocks can include polymers and oligomers of hydroxy acids or other biologically degradable polymers that yield materials that are non-toxic or present as normal metabolites in the body. Preferred poly(hydroxy acid)s are poly(glycolic acid), poly(DL-lactic acid) and poly(L-lactic acid). Other useful materials include poly(amino acids), poly(anhydrides), poly(orthoesters), and poly (phosphoesters). Polylactones such as poly(epsilon-caprolactone), poly(delta-valerolactone), poly(gamma-butyrolactone)and poly (beta-hydroxybutyrate), for example, are also useful.

Biodegradable regions can be constructed from monomers, oligomers or polymers using linkages susceptible to biodegradation, such as ester, peptide, anhydride, orthoester, and phosphoester bonds.

By varying the total amount of biodegradable groups, and selecting the ratio between the number of carbonate or dioxanone linkages (which are relatively slow to hydrolyze) and of lower hydroxy acid linkages (especially glycolide or lactide, which hydrolyze relatively rapidly), the degradation time of hydrogels formed from the macromers can be controlled.

Carbonates and Dioxanones

Any carbonate can be used to make the macromers. Preferred carbonates are aliphatic carbonates, for maximum biocompatibility. For example, trimethylene carbonate and dimethyl carbonate are examples of aliphatic carbonates. Lower dialkyl carbonates are joined to backbone polymers by removal by distillation of alcohols formed by equilibration of dialkyl carbonates with hydroxyl groups of the polymer.

More preferred carbonates are the cyclic carbonates, which can react with hydroxy-terminated polymers without release of water. Suitable cyclic carbonates include ethylene carbonate (1,3-dioxolan-2-one), propylene carbonate (4-methyl -1,3-dioxolan-2-one), trimethylene carbonate (1,3-dioxan-2-one) and tetramethylene carbonate (1,3-dioxepan-2-one). Under some reaction conditions, it is possible that orthocarbonates may react to give carbonates, or that carbonates may react with polyols via orthocarbonate intermediates, as described in Timberlake et al, U.S. Pat. No. 4,330,481. Thus, certain orthocarbonates, particularly dicyclic orthocarbonates, can be suitable starting materials for forming the carbonate-linked macromers.

Alternatively, suitable diols or polyols, including backbone polymers, can be activated with phosgene to form chloroformates, as is described in the art, and these active compounds can be mixed with backbone polymers containing suitable groups, such as hydroxyl groups, to form macromers containing carbonate linkages.

All of these materials are "carbonates" as used herein.

Suitable dioxanones include dioxanone (p-dioxanone; 1,4-dioxan-2-one; 2-keto-1,4-dioxane), and the closely related materials 1,4-dioxolan-2-one, 1,4-dioxepan-2-one and 1,5-dioxepan-2-one. Lower alkyl, for example C1–C4 alkyl, derivatives of these compounds are also contemplated, such as 2-methyl p-dioxanone (cyclic O-hydroxyethyl ether of lactic acid).

Polymerizable Groups

The term "polymerizable group" is defined as a reactive functional group that has the capacity to form additional covalent bonds resulting in macromer interlinking. Polymerizable groups specifically include groups capable of polymerizing via free radical polymerization and groups capable of polymerizing via cationic or heterolytic polymerization. Suitable groups include, but are not limited to, ethylenically or acetylenically unsaturated groups, isocyanates, epoxides (oxiranes), sulfhydryls, succinimides, maleimides, amines, imines, anides, carboxylic acids, sulfonic acids and phosphate groups. (Aliphatic hydroxy groups are not considered to be reactive groups for the chemistry disclosed herein, except in formulations which also contain groups capable of covalent crosslinking with such hydroxyls.) Ethylenically unsaturated groups include vinyl groups such as vinyl ethers, N-vinyl amides, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. Unsaturated tricarboxylic acids include aconitic acid. Polymerizable groups may also be derivatives of such materials, such as acrylamide, N-isopropylacrylamide, hydroxyethylacrylate, hydroxyethylmethacrylate, and analogous vinyl and allyl compounds. Reactive group forming compounds will preferably be available in a stable activated form, to allow simple incorporation into the macromer. Examples of such materials are (meth)acrylyl chloride, acrylic anhydride, and allyl glycidyl ether. The polymerizable groups are preferably located at one or more ends of the macromer. In a less preferred embodiment, the polymerizable groups can be located within the macromer.

Polymerization is initiated by any convenient reaction, including photopolymerization, chemical or thermal free-radical polymerization, redox reactions, cationic polymerization, and chemical reaction of active groups (such as isocyanates, for example.) Polymerization is preferably initiated using photoinitiators. Photoinitiators that generate a free radical or a cation on exposure to UV light are well known to those of skill in the art. Free-radicals can also be formed in a relatively mild manner from photon absorption of certain dyes and chemical compounds. The polymerizable groups are preferably polymerized by free radical polymerization. The preferred polymerizable groups are acrylates, diacrylates, oligoacrylates, methacrylates, dimethacrylates, oligomethacrylates, cinnamates, dicinnamates, oligocinnamates, and other biologically acceptable photopolymerizable groups.

These groups can be polymerized using photoinitiators that generate free radicals upon exposure to light, including UV (ultraviolet) and IR (infrared) light, preferably long-wavelength ultraviolet light (LWUV) or visible light. LWUV and visible light are preferred because they cause less damage to tissue and other biological materials than short-wave UV light. Useful photoinitiators are those which can be used to initiate polymerization of the macromers without cytotoxicity and within a short time frame, minutes at most and most preferably seconds.

Exposure of dyes, preferably in combination with co-catalysts such as amine, to light, preferably visible or LWUV light, can generate free radicals. Light absorption by the dye causes the dye to assume a triplet state, and the triplet state subsequently reacts with the amine to form a free radical which initiates polymerization, either directly or via a suitable electron transfer reagent or co-catalyst, such as an amine. Polymerization can be initiated by irradiation with light at a wavelength of between about 200–1200 nm, most preferably in the long wavelength ultraviolet range or visible range, 320 nm or higher, and most preferably between about 365 and 550 nm.

Numerous dyes can be used for photopolymerization. Suitable dyes are well known to those of skill in the art. Preferred dyes include erythrosin, phloxime, rose bengal, thionine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

Suitable chemical, thermal and redox systems may initiate the polymerization of unsaturated groups by generation of free radicals in the initiator molecules, followed by transfer of these free radicals to the unsaturated groups to initiate a chain reaction. Peroxides and other peroxygen compounds are well-known in this regard, and may be considered as chemical or thermal initiators. Azobisbutyronitrile is a chemical initiator. A combination of a transition metal, especially iron, with a peroxygen and preferably a stabilizing agent such as glucuronic acid allows generation of free radicals to initiate polymerization by a cycling redox reaction.

Combinations of chemical or redox systems with photo-initiated systems have been demonstrated to be effective in WO 96/29370, and are a preferred initiation system for many applications of the macromers of the present invention.

It is also possible to use the macromers with other types of linking reactions. For example, a macromer could be constructed with amine termination, with the amine considered as an active group; and another macromer could be constructed with isocyanate termination, with the isocyanate as the active group. On mixing, the materials will spontaneously react to form a gel. Alternatively, an isocyanate-terminated macromer could be polymerized and crosslinked with a mixture of diamines and triamines. Such a reaction is more difficult to control than a photoinitiated reaction, but could be preferred for high volume extracorporeal production of gels for implantation, perhaps as drug delivery systems. Other pairs of reactants include maleimides with amines or sulfhydryls, or oxiranes with amines, sulfhydryls or hydroxyls.

Preferred Macromers

Preferably, the macromers contain between about 0.3% and 20% by weight of carbonate residues or dioxanone residues, more preferably, between about 0.5% and 15% carbonate or dioxanone residues, and most preferably, about 1% to 5% carbonate or dioxanone residues. In those embodiments where hydroxy acid residues are desired, the macromer contains between about 0.1 and 10 residues per residue of carbonate or dioxanone, more preferably between about 0.2 and 5, and most preferably one or more such residue per macromer.

In a preferred embodiment, the macromer includes a core, an extension on each end of the core, and an end cap on each extension. The core is a hydrophilic polymer or oligomer; each extension is a biodegradable oligomer comprising one or more carbonate or dioxanone linkage; and each end cap comprises one or more functional groups capable of cross-linking the macromers. In a particularly preferred embodiment, the core includes hydrophilic poly(ethylene glycol) oligomers with a molecular weight between about 400 and 40,000 Da; each extension includes 1 to 10 residues selected from carbonate and dioxanone, and optionally further included between one and five hydroxyacid residues, preferably alpha-hydroxy acid residues; wherein the total of all residues in the extensions is sufficiently small to preserve water-solubility of the macromer, being typically less than about 20% of the weight of the macromer, more preferably 10% or less.

Preferably, each end cap includes a polymerizable group. The preferred groups are free-radical (homolytically) polymerizable. More preferably, they are ethylenically-unsaturated (i.e., containing carbon-carbon double bonds), with a preferred molecular weight between about 50 and 300 Da, which are capable of cross-linking and/or polymerizing the macromers. A preferred embodiment incorporates a core consisting of poly(ethylene glycol) oligomers of molecular weight about 25,000 Da; extensions including polycarbonate or poly(dioxanone) oligomers with a molecular weight of about 200 to 1000 D, alone or in combination with extensions formed of hydroxy acid oligomers; and end caps consisting of acrylate moieties (which are about 55 Da molecular weight).

Macromer Synthesis

The macromers can be synthesized using means well known to those of skill in the art. General synthetic methods are found in the literature, for example in U.S. Pat. No. 5,410,016 to Hubbell et al., U.S. Pat. No. 4,243,775 to Rosensaft et al., and U.S. Pat. No. 4,526,938 to Churchill et al.

For example, a polyethylene glycol backbone can be reacted with trimethylene carbonate (TMC) or a similar carbonate in the presence of a Lewis acid catalyst, such as stannous octoate, to form a TMC-polyethylene glycol terpolymer. The TMC-PEG polymer may optionally be further derivatized with additional degradable groups, such as lactate groups. The terminal hydroxyl groups can then be reacted with acryloyl chloride in the presence of a tertiary amine to end-cap the polymer with acrylate end-groups. Similar coupling chemistry can be employed for macromers containing other water-soluble blocks, biodegradable blocks, and polymerizable groups, particularly those containing hydroxyl groups.

When polyethylene glycol is reacted with TMC and a hydroxy acid in the presence of an acidic catalyst, the reaction can be either simultaneous or sequential. As shown in the examples below, the simultaneous reaction will produce an at least partially random copolymer of the three components. Sequential addition of a hydroxy acid after reaction of the PEG with the TMC will tend to produce an inner copolymer of TMC and one or more PEGs, which will statistically contain more than one PEG residue linked by linkages derived from TMC, with hydroxy acid largely at the ends of the (TMC, PEG) region. There is a tendency for TM and other carbonate groups to re-arrange by "back-biting" during synthesis, which is why multiple PEG molecules can become incorporated in the same macromer. When the hydroxy acid contains a secondary hydroxyl, as in lactic acid, then the tendency towards rearrangement is reduced.

In principle, the degradable blocks or regions could be separately synthesized and then coupled to the backbone regions. In practice, this more complex reaction does not appear to be required to obtain useful materials.

Sequential Addition

In a preferred embodiment, sequential addition of biodegradable groups to a carbonate-containing macromer can be used to enhance biodegradability of the macromer after capping with reactive end groups.

Upon reaction of, for example, trimethylene carbonate (TMC) with polyethylene glycol (PEG), the TMC linkages in the resulting copolymers have been shown to form end linked species of PEG, resulting in segmented copolymers, i.e. PEG units coupled by one or more adjacent TMC linkages. The length of the TMC segments can vary, and is believed to exhibit a statistical distribution. Coupling may also be accomplished via the carbonate subunit of TMC. These segmented PEG/TMC copolymers form as a result of transesterification reactions involving the carbonate linkages of the TMC segments during the TMC polymerization process when a PEG diol is used as an initiator. Similar behavior is expected if other polyalkylene glycol initiators were used. The end-linking may begin during the reaction of the TMC with the PEG, and completion of the end linking and attainment of equilibrium is observable by a cessation of increase of the viscosity of the solution.

If the product of this first reaction step is then reacted with a reactive end-capping material, such as acryloyl chloride, a significant percentage of the macromer end groups can be PEG hydroxyls, resulting in the attachment of the reactive groups directly to one end of a non-biodegradable PEG molecule. Such a reaction of the PEG/TMC segmented copolymers can be prevented by adding additional segments of other hydrolyzable co-monomers (e.g. lactate, glycolate, 1,4-dioxanone, dioxepanone, caprolactone) on either end of the PEG/TMC segmented copolymer. Some scrambling of the comonomer segments with the PEG/TMC prepolymer is expected, but this can be minimized by using proper reaction conditions. The basic PEG/TMC segmented copolymer or the further reacted PEG/TMC/comonomer segmented terpolymer is then further reacted to form crosslinkable macromers by affixing reactive end groups (such as acrylates) to provide a macromer with reactive functionality. Subsequent reaction of the end groups in an aqueous environment results in a bioabsorbable hydrogel. Similar segmented structures would be expected if another polyalkylene glycol (PAG) were used, for example a poloxamer.

The copolymers and macromers can have tailorable solubility and solution viscosity properties. The hydrogels can have tailorable modulus and degradation rate. For a given solution concentration in water, the viscosity is affected by the degree of end linking, the length of the TMC (and other hydrophobic species) segments, and the molecular weight of the starting PAG. The modulus of the hydrogel is affected by the molecular weight between crosslinks. The hydrogel degradation rate can be modified by adding a second, more easily hydrolyzed comonomer (e.g. lactate, glycolate, 1,4-dioxanone) as a segment on the ends of the basic PAG/TMC copolymer prior to adding the crosslinkable end group to form the macromer.

Some of these structures described herein are depicted below. PEG, lactate and acrylate units are used solely for purposes of illustration.

SOME BASIC STRUCTURES:

$(CH_2—CH_2—O)_x$=PEG repeat unit=$(PEG)_x$
$(CO—(CH_2)_3—O)_y$=TMC repeat unit=$(TMC)_y$
$(CO—CH(CH_3)—O)_z$=Lactate repeat unit=$(LA)_z$
$—CO—CH=CH_2$=Acrylate end group=AA

SEGMENTED PEG/TMC COPOLYMER:

$HO—(CO—(CH_2)_3—O)_y—[(CH_2—CH_2—O)_x—(CO—(CH_2)_3—O)_y]_n—H$ or $HO—(TMC)y—[(PEG)x—(TMC)y]n—H$

SEGMENTED PEG/TMC/Lactate TERPOLYMER:

$HO—(CH(CH3)—CO)_z—O—(CO—(CH_2)_3—O)_y—[(CH_2—CH_2—O)_x—(CO—(CH_2)_3—O)_y]_n—(CO—CH(CH_3)—O)_z—H$ or $HO—(LA)_z—(TMC)_y—[(PEG)_x—(TMC)_y]_n—(LA)_z—H$

SEGMENTED PEG/TMC MACROMER (acrylated):

$CH_2=CH—CO—O—(CO—(CH_2)_3—O)_y[(CH_2—CH_2—O)_x—(CO—(CH_2)_3—O)_y]_n—CO—CH=CH_2$ or $AA—(TMC)_y—[(PEG)_x—(TMC)_y]_n—AA$

SEGMENTED PEG/TMC/Lactate TERPOLYMER MACROMER (acrylated):

$AA—(LA)_z—(TMC)_y—[(PEG)_x—(TMC)_y]_n—(LA)_z—AA$

Applications for the Macromers

Sealing Leaks in Tissue

A preferred application of the polymers is in a method of sealing leaks, for example, leaks of gases and/or bodily fluids (such as blood, cerebrospinal fluid, urine and bile), in tissue such as lung, urethra, ureter, gastrointestinal tract, reproductive tract, liver, spleen, dura, and the spinal cord. The method involves priming the surface of the tissue with a polymerization initiator, applying a macromer solution that also contains one or more polymerization initiators to the surface of the tissue to be coated, and then polymerizing the macromer. Preferably, the polymerization initiator comprises a photoinitiator.

Applying the initiator to surface of the tissue before adding the macromer solution polymerizes the macromer at the interface between the solution and the tissue surface. This "interfacial polymerization" provides excellent adherence of the resulting polymer to the tissue surface. Providing an initiator in the macromer solution allows a relatively thick, for example 1 mm to 10 mm, layer of polymer to be formed on the tissue surface. Relatively thick polymer layers may be required to effectively seal some types of tissue, for example, lung tissue or dura, depending on the size of the leak.

An advantage of the macromers when prepared with at least one carbonate group is that during the synthesis of the macromer, short blocks of non-biodegradable but excretable polymer, such as polyethylene oxide chains of up to about 40,000 D, can become linked by carbonate groups to give higher molecular weights to the macromers while preserving the biodegradability to secretable products of the macromer. It is believed that the higher molecular weights increase the elasticity of the final hydrogel. This is an important and useful property when the polymer must be readily and repeatedly stretched, as in a sealant layer applied to lung tissue. High elasticity can also be provided by linking nondegradable blocks with other polyfunctional linkers, such as dicarboxylic acids. However, since the synthetic chemistry required to make such macromers can be more complex than the simple reactions required for carbonate-based linking, this method is less preferred.

Prevention of Surgical Adhesions

Another preferred application is a method of reducing formation of adhesions after a surgical procedure in a patient. The method involves coating damaged tissue surfaces in a patient with an aqueous solution of a light-sensitive free-radical polymerization initiator and a macromer solution as described above. The coated tissue surfaces are exposed to light sufficient to polymerize the macromer. The light-sensitive free-radical polymerization initiator may be a single compound (e.g., 2,2-dimethoxy-2-phenyl acetophenone) or a combination of a dye and a cocatalyst (e.g., ethyl eosin or eosin Y, and triethanolamine).

Controlled Delivery of Incorporated Agents

Another preferred application involves locally applying an incorporated agent, such as a prophylactic, therapeutic or diagnostic agent, to tissue surfaces of a patient. The method includes the steps of mixing an agent to be incorporated with an aqueous solution including a suitable polymerization initiator, such as a light-sensitive free-radical polymerization initiator, and a macromer, to form a coating mixture. Tissue surfaces are coated with the coating mixture and the macromer is polymerized, for example, by exposure of the coating mixture to an effective amount of light of an appropriate wavelength.

Any of a variety of therapeutic, prophylactic or diagnostic agents can be delivered using these methods. Examples include synthetic and natural inorganic and organic compounds such as proteins (100 amino acid residues or more), peptides (less than 100 amino acid residues), carbohydrates, lipids, nucleic acid molecules, and small synthetic materials such as ethical drugs, having therapeutic, prophylactic or diagnostic activities. Nucleic acid molecules include genes, antisense molecules which bind to complementary DNA to inhibit transcription, aptamers, triple helix forming oligomers and ribozymes. The agents to be delivered can have a variety of biological activities. Diagnostic agents such as radiolabelled compounds, enzymatically labeled compounds, fluorescently labeled compounds, and other detectable agents can also be incorporated. Compounds with a wide range of molecular weights can be incorporated, for example, between 100 and 500,000 grams or more per mole.

Therapeutic or prophylactic compounds ("drugs") of particular interest are those whose efficacy in treatment of a localized medical condition is increased by local delivery of the compound at or near the site of the localized medical condition. Examples of classes of such drugs are those which inhibit the formation or reformation of scars or adhesions; those which prevent unwanted proliferation of vascular tissue or other luminal tissue; and growth factors, cytokines, etc. which only needs to be effective locally.

Imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Hydrogels incorporating these agents can be detected using standard techniques available in the art and commercially available equipment.

The macromers are particularly useful for delivering hydrophilic and/or labile materials. Because the macromer is water-soluble, water can penetrate the polymer and dissolve or extract incorporated hydrophilic materials. Labile materials can be incorporated without exposure of the material to organic solvents which would destroy biological activity. Hydrophobic materials may also be incorporated, if the rate of dissolution of the hydrophobic material and/or the gel matrix is sufficiently rapid to release the material at a therapeutically-effective rate. In all cases, the polymerized hydrogel will tend to protect the therapeutic material from attack by biological activities of the subject, such as enzyme activity.

In a variation of the method for controlled drug delivery, the macromers are polymerized with incorporated

Preferred Macromers

Preferably, the macromers contain between about 0.3% and 20% by weight of carbonate residues or dioxanone residues, more preferably, between about 0.5% and 15% carbonate or dioxanone residues, and most preferably, about 1% to 5% carbonate or dioxanone residues. In those embodiments where hydroxy acid residues are desired, the macromer contains between about 0.1 and 10 residues per residue of carbonate or dioxanone, more preferably between about 0.2 and 5, and most preferably one or more such residue per macromer.

In a preferred embodiment, the macromer includes a core, an extension on each end of the core, and an end cap on each extension. The core is a hydrophilic polymer or oligomer; each extension is a biodegradable oligomer comprising one or more carbonate or dioxanone linkage; and each end cap comprises one or more functional groups capable of cross-linking the macromers. In a particularly preferred embodiment, the core includes hydrophilic poly(ethylene glycol) oligomers with a molecular weight between about 400 and 40,000 Da; each extension includes 1 to 10 residues selected from carbonate and dioxanone, and optionally further includes between one and five hydroxyacid residues, preferably alpha-hydroxy acid residues; wherein the total of all residues in the extensions is sufficiently small to preserve water-solubility of the macromer, being typically less than about 20% of the weight of the macromer, more preferably 10% or less.

Preferably, each end cap includes a polymerizable group. The preferred groups are free-radical (homolytically) polymerizable. More preferably, they are ethylenically-unsaturated (i.e., containing carbon-carbon double bonds), with a preferred molecular weight between about 50 and 300 Da, which are capable of cross-linking and/or polymerizing the macromers. A preferred embodiment incorporates a core consisting of poly(ethylene glycol) oligomers of molecular weight about 25,000 Da; extensions including polycarbonate or poly(dioxanone) oligomers with a molecular weight of about 200 to 1000 D, alone or in combination with extensions formed of hydroxy acid oligomers; and end caps consisting of acrylate moieties (which are about 55 Da molecular weight).

Tissue Adhesives

The macromers, and hydrogels formed therefrom, can also be used to adhere tissue surfaces in a patient. The macromer is mixed with a suitable polymerization initiator system, such as a photoinitiator or photoinitiator/amine mixture, to form an aqueous mixture. The mixture is applied to a tissue surface to which tissue adhesion is desired. The tissue surface is contacted with the tissue with which adhesion is desired, forming a tissue junction. The macromers are then polymerized at the tissue junction.

Such a technique can be used to hold surgically severed tissue in apposition during the healing process, thereby replacing or supplementing the use of sutures, staples, etc. In addition, such a gel may also be used to form a protective barrier.

Tissue Coatings

In a particularly preferred application of these macromers, an ultra thin coating is applied to the surface of a tissue, most preferably the inside surface of a blood vessel. Such coatings can be used to treat or prevent stenosis or restenosis of blood vessels. A polymerization initiator, preferably a photoinitiator, is applied to the surface of the tissue, allowed to stain the tissue, and, optionally, the excess photoinitiator is removed by dilution or rinsing. After the initiator has been applied to the tissue, the macromer solution is applied and the macromer is polymerized. As demonstrated below, this method is capable of creating a uniform polymeric coating of between about one and 300 microns in thickness, more preferably about ten to 200 microns, most preferably 20 to 80 microns, which does not evoke thrombosis during its residence at the site.

Coating Medical Devices

The surface of medical devices can be coated with the macromers using interfacial polymerization, bulk polymerization, or both, as discussed above. Coating layers applied using interfacial polymerization or a combination of interfacial and bulk polymerization typically adhere more strongly to the medical devices than those prepared using only bulk polymerization.

The present invention will be more fully understood by reference to the following non-limiting examples.

EXAMPLE 1

General Synthesis of Macromers: Melt Method

Methods analogous to those described in U.S. Pat. No. 4,526,938 to Churchill et al. were used to form derivatized PEG by the melt method. Polyethylene glycol (PEG) was obtained commercially. The molecular weight listed on the label was assumed to be the molecular weight of the material. The PEG was optionally dissolved in methanol and purified by passage over an ion exchange resin, and dried.

Purified or as-supplied PEG was charged to a reactor, optionally with a small amount of xylene, and heated for five to six hours at about 110° C. (note: all temperatures herein are in degrees Celsius) under vacuum to complete removal of water. After cooling under vacuum, the flask was placed in a glove bag, the materials for forming the biodegradable linkages (including T (trimethylene carbonate) and L (lactide)) were added to the PEG, and the temperature was raised to about 160–165° C. under an argon blanket.

After dissolution of the reactants in the melted PEG, a catalyst, typically stannous octoate, was added, the temperature was raised to 185° C., and ring-opening addition was allowed to proceed for about 3 hours, with stirring under argon. The PEG-(T,L) intermediate could be further reacted at this stage, but typically was freed of unreacted monomers by precipitation in hexane, recovery and drying.

The purified intermediate, for example, PEG-(TnLm), where "n" is the number of T groups and "m" is the number of L groups, or the original reaction mixture without purification, was taken up in toluene, and an agent capable of adding unsaturated linkages, such as acryloyl chloride, was added, typically in excess, under mild heating (e.g., about 50° C.) and in the presence of an acid-neutralizing agent such as triethylamine. Suitable reactant ratios were found to be 1 ml acryloyl chloride and 1.8 ml triethylamine per 30 grams of PEG. The endcapped macromer, PEG-(T, L)-A2, was purified by precipitation in hexane, recovered and dried. Stabilizer was optionally added at this stage. The extent of incorporation of monomers was determined by NMR.

A similar procedure was used to prepare other macromers. PEG-(Tn)-A2, PEG-(Dn, Gm)-A2, where D is dioxanone and G is glycolide, and like materials were formed by similar procedures. Synthesis of macromers based on other starting hydrophilic blocks follows similar procedures, with adjustment in precipitation conditions as required. In a synthesis with multi-hydroxy compounds, such as polyvinyl alcohol, the water would be removed azeotropically under mild reflux in, e.g., toluene; and the degradable linkages are preferably synthesized by polymerization onto the hydroxy compound as described above, although such blocks could be added as preformed activated acrylated blocks, for example, using a carbodiimide derivative of the acylated poly(degradable linkage), if greater control were required.

EXAMPLE 2

Synthesis of PEG-TMC and PEG-TMC-Lactide Macromers

35K(T8)A2 ("35KT" in the examples below) was made from purified PEG of nominal molecular weight 35,000 by the melt procedure as described above. T was charged into the reactor at a nominal molar ratio of 13:1 to the PEG to obtain this result. The final actual acrylate incorporation averaged 1.6 per PEG molecule, or about 2 acrylates per macromer.

35K(T7L2)A2 ("35KTL") contained about 7 T units (6.88 measured) and 2 lactate units (1.86 measured) as synthesized. (Note that there are 2 lactate units per lactide molecule.) T and L were charged at nominal molar ratios of 10:1 and 3:1 relative to PEG.

20K(T30L15)A2 contained about 30 T units and 15 lactide units per 20,000 D PEG molecule. The actual acrylate to PEG ratio was 1.42.

EXAMPLE 3

Seal Pressure Test on Latex to Measure Strength and Elasticity

Poly(ethylene glycol)-lactide-trimethylene carbonate terpolymers endcapped with acrylate esters were evaluated using a seal pressure test apparatus to determine the failure pressure for coatings prepared using the macromers.

One of the materials tested had a poly(ethylene glycol) molecular weight of 20,000 Daltons ("20 kD"), a lactate incorporation of 13.8 and a trimethylene carbonate incorporation of 16.0, with nominal acrylation of 2 per macromer ("20KTL"). Also tested were 35 kD PEG esterified with about 8 TMC linkages and then endcapped with acrylates ("35KT"), and 35 kD PEG esterified with about 8 TMC and about 8 lactate groups ("35 KTL"), both also acrylated. The reagents applied were "primer" and "sealant". The complete system contained both a photoinitiation system (Eosin Y/triethanolamine) and a redox initiation system (ferrous gluconate/fructose, plus t-butylhydroperoxide after mixing) which did not cause significant polymerization of the macromer until both mixed (primer and sealant) and activated by light.

Primer solution contained Eosin Y (2000 ppm, w/w), 5000 ppm ferrous gluconate, 10,000 ppm (1%) fructose, 30,000 ppm NaCl, and 30% w/w of 3.5KL5 macromer (made according to U.S. Pat. No. 5,410,016). Primer was applied to a 2 cm×2 cm piece of latex film (from a latex examination glove; about 1 mm thick) with a 6 mm diameter hole created in the center. A toroidal Teflon® fluoropolymer template with a 1 cm. diameter central hole was placed on the latex film to control the area of application of the sealant, by limiting its spread.

Sealant solution contained macromer (in this example, 10% or 20% w/w of one of the macromers described above) dissolved in an aqueous solution containing isotonic saline, 90 mM triethanolamine as buffer and electron transfer component, Eosin Y (20 ppm) as a photoinitiator, 4000 ppm vinylcaprolactam as comonomer, and 125 ppm t-butylhydroperoxide as part of the light-sensitized redox initiation system. Two drops of sealant were dispensed inside the template above the hole and then carefully mixed in with the primer, using a brush. Three more drops of sealant were dispensed, and then the area was illuminated with visible light from a xenon arc lamp (450–550 nm) at an intensity of 100 mW/cm$^2$ for 40 seconds. Samples were placed in phosphate buffered saline (pH 7.4) at 37° C. for different times (t=0, 4 hours, 1 days, 3 days, 6 days and 10 days).

Samples were evaluated at each time point using a seal pressure test apparatus to determine the failure pressure. The test apparatus was a modified membrane holder, in which the latex sample was clamped at the edges between gaskets. Pressure was then applied to the side of the latex away from the polymer seal, and the pressure required to rupture the seal was measured.

FIG. 1 shows the results obtained with five different sealant materials. The seal pressure decreases over the course of time, presumably due to a combination of swelling of the hydrogel due to hydration and programmed degradation of the hydrogel.

EXAMPLE 4

Bioabsorption In-Vivo

Poly(ethylene glycol)-trimethylene carbonate copolymers, optionally containing lactate, and endcapped with acrylate esters, were evaluated. Two of the materials described in Example 3 were used (20KTL and 35KT). The macromers were polymerized using visible light illumination from a xenon arc lamp (450–550 nm) at an intensity of 100 mW/cm$^2$ in a sealant solution containing macromer, eosin, triethanolamine, vinylcaprolactam, t-butylhydroperoxide and saline as in Example 3. Macromer concentration was 10% for 20KTL and 20% for 35KT.

The absorption of the sealant was determined by subcutaneous implants in rats. Five female Sprague Dawley rats (250–300 g) were used in this study. The animals were anesthetized by intramuscular ("IM") injection of 3.2 ml/kg mixture of Ketamine (52.4 mg/kg), Xylazine (2.8 mg/kg), Acepromazine (0.7 mg/kg). Four 1 cm longitudinal incisions were made through the skin on the back. Two incisions were made on each side of the spinal column, spaced 1 cm off the midline and 2 cm apart. A 2×2 cm pocket was created at each incision site by blunt dissection. Preformed hydrogel disks were prepared using sterile technique. One hundred microliters of sealant solution was placed in the bottom of one well of a standard 24-well tissue culture plate, and was illuminated for 40 sec at 100 mW/cm$^2$, producing a thin disc about 18 mm. in diameter. One disk was placed in each subcutaneous pocket. Incisions were then closed with surgical staples. Animals were euthanized at intervals by $CO_2$ inhalation. Incisions were opened and gross observations were recorded. Each site was harvested and analyzed by gel permeation chromatography for mass loss.

Figure 2A:
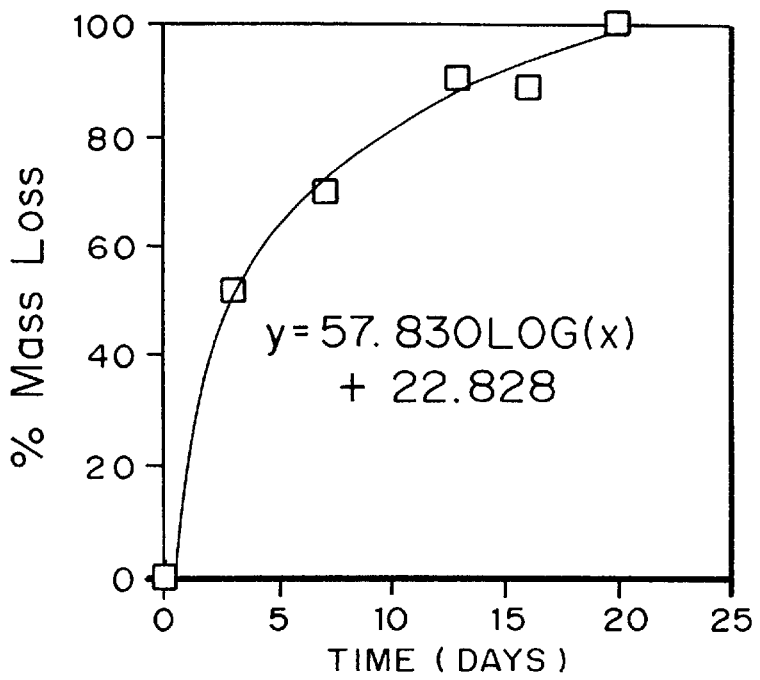
FIGS. 2A and 2B are graphs of the degradation (% mass loss) over time (days) for 20K T (FIG. 2A) and 35K T (FIG. 2B) for subcutaneous polymeric implants in rats.
Figure 2B:
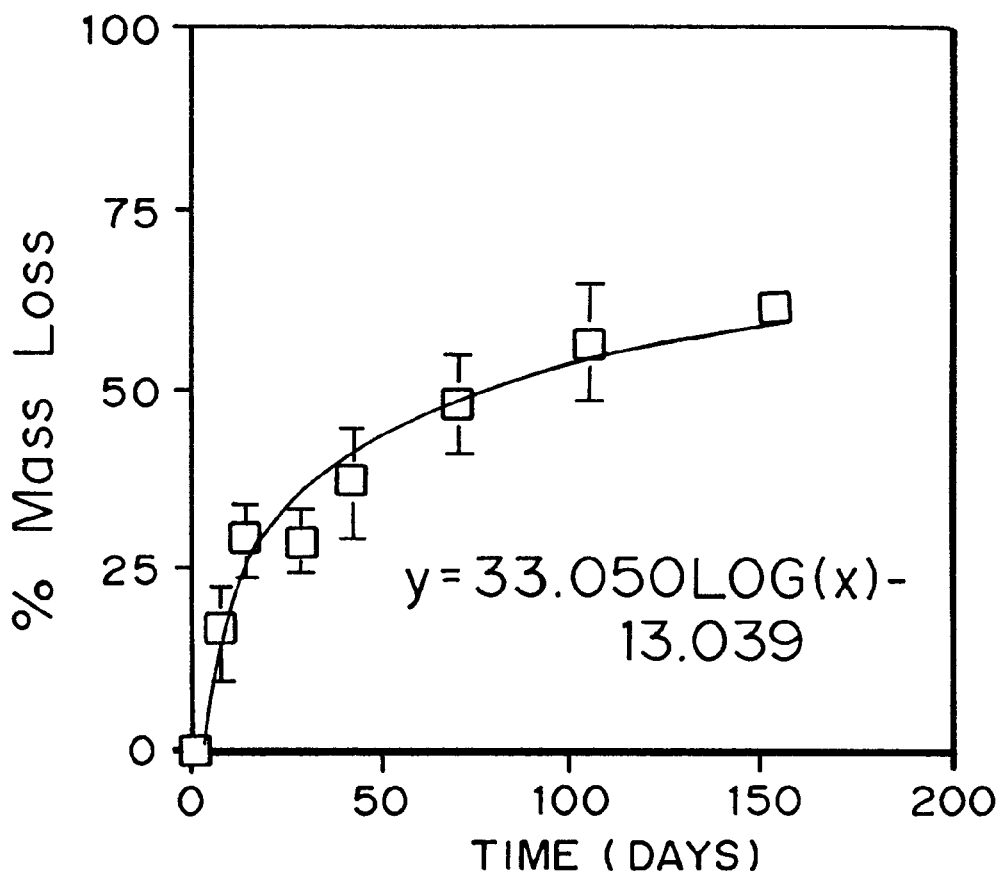

FIGS. 2A and 2B show that the 20KTL based hydrogels were completely absorbed in 20 days in vivo (FIG. 2A), whereas the 35KT based hydrogels were partially absorbed (60% weight loss) in 154 days (FIG. 2B). This illustrates the significant effect of rapidly-degrading linkages such as lactate groups.

EXAMPLE 5

Sealing of Dural Leak in Canine Craniotomy

A poly(ethylene glycol)-trimethylene carbonate-lactate copolymer endcapped with acrylate ester (20KTL, from Example 2) was evaluated for its ability to seal fluid leaks in membranes in vivo. The poly(ethylene glycol) molecular weight used was 20,000 Da. The lactate incorporation was 13.8 and the trimethylene carbonate incorporation was 16.0. The macromer was fully acrylated.

The performance of the sealant was evaluated in a dural incision injury model in three mongrel canines. The animals were pre-anesthetized, intubated and maintained on isoflurane gas anesthesia. With the head elevated, a bilateral craniotomy was created. Two dural incisions, each 2 cm. long, were made, one on the left side and one on the right side. Incisions were closed using 3 simple interrupted 4-0 to 6-0 silk sutures spaced approximately 5 mm apart. Cerebrospinal fluid (CSF) pressure was raised by inflating the lungs to 20 cm $H_2O$, and the leak was assessed. All incisions were found to leak, as expected from the closure.

The control side (left) received no additional closure of the incision. For the treatment side (right), the primer (a low-viscosity solution; described in example 4) was applied and mixed with the fluid on the tissue interface. The sealant (10% w/w solution of 20KTL (described above) with other materials as in Example 4) was layered over the primer, and the primer and sealant were mixed with a brush. Illumination for 40 sec. with a visible xenon arc lamp (450–550 nm) at an intensity of 100 mW/cm$^2$ was then performed to complete the polymerization.

The leaks were re-verified by raising the CSF pressure by inflating the lungs to 20 cm $H_2O$. Leakage was observed on the control side, but not on the experimental side. The bone flaps were replaced and the incision was repaired.

All animals were euthanized at 21 days and the craniotomy was re-opened. Adhesions between the dura and the bone flap were recorded, and the dura repair sites were inspected for evidence of CSF fluid leaks. Dural repair sites were dissected free from underlying cortical tissue and the presence of adhesions noted. The tissues were harvested, rinsed in saline, and fixed in 10% neutral buffered formalin. Hematoxylin and eosin stained histological sections were taken.

At the time of explant, the control sites showed a slight fibrosis present between the dura mater and calvarium. No inflammation was detected. The sealant was not apparent in two out of three animals and only small amounts were present in the third animal. The dural edges were approximated. Defects in the bone (resulting from the surgery) were filled with fibro-osseous tissue at 21 days, in both control and treated sites. Normal healing appeared to be taking place, both visually and histologically.

EXAMPLE 6

Solution Synthesis

Macromers can also be made by synthesis in solution. While requiring additional waste disposal, the solution synthesis is more easily controlled (compared to the melt synthesis of Example 1 or 2), and is preferred for most applications. This example also illustrates the practice of sequential addition of monomers; the method is also useful for simultaneous addition of monomers.

35KTLA was made by dissolving 75 g of 35kD (nominal) PEG in toluene to 20% w/w concentration, and was dried by nitrogen purge for 3 hours at 108° C. 3.06 G TMC (14 mole equivalents per PEG) and 0.024 g stannous octoate catalyst were added, and the solution was held at 108° for 4 hours with stirring. Then 0.46 g (1.5 equiv.) lactide was added, and stirring continued for 2 hrs. Then 300 ml toluene was added to give about a 10% wt/vol solution of polymer. After cooling the solution to about 50°, 4.6 g of triethylamine and 2.5 ml of acryloyl chloride were added. The solution was stirred for 20 min. at about 50. Acrylated macromer was recovered by precipitation and optionally filtration as described in Ex. 1 and 2. The resulting polymer contained 5 TMC residues and 1.2 lactate residues per PEG molecule, and ratios of lactate:acrylate of 0.6.

EXAMPLE 7

In Vitro Degradation

35KTLA2 was synthesized as described in Example 6. The completed macromer had a TMC:PEG molar ratio of 3.57; an acrylate: PEG ratio of 1.52; a lactate: PEG ratio of 1.39; and contained 766 ppm TMC. On gel permeation chromatography, the macromer was 48.1% "monomer" (one PEG unit per macromer molecule), 46.3% "dimer" two PEG units per macromer molecule), 5.4% "trimer" and 0.1% higher oligomer.

Discs of the macromer were made as described in example 4 and were incubated in phosphate-buffered saline, pH 7.4, at 37° and 57°. At 57°, half of the mass was lost at about 140 hrs, while at 37°, half the mass was lost at about 42 days. Mass loss was determined by rinsing the specimen, drying to constant weight, and correcting for the amount of buffer and salt present.

EXAMPLE 8

Dioxanone-Containing Macromers

Dioxanone (1,4-dioxan-2-one; p-dioxanone) was synthesized from DEG (diethylene glycol) essentially according to U.S. Pat. No. 2,807,629, Example 1. Two kilograms of DEG were mixed with 40 g. copper chromite (Aldrich) and heated at about 230° for 4 hours under nitrogen purge, which displaced generated hydrogen. Dioxanone and DEG were distilled from the mixture under vacuum at about 50° pot temperature. DEG was partially removed by extraction in cold (4°) diethyl ether. The partially purified material was dissolved in chloroform and applied to a silica column equilibrated in chloroform. Dioxanone was recovered in the initial fractions.

Macromer 35KDA was made by drying overnight (vacuum, 110°) 15 g of 35K PEG, 1.7 g dioxanone, and 0.01 g of catalyst (stannous octoate). This is a ratio of 21:1 D:PEG. Samples were also made at other amounts of D (1.0 g, 18:1; 0.84 g, 15:1; 1.34 g, 24:1). Vials were sealed and heated at 150 for 5 hrs. Samples were dissolved in chloroform; optionally precipitated in ether; and acrylated as described in previous examples. NMR showed final molar ratios in the synthesized polymer of D/PEG, 1.82; Ac/PEG, 1.64.

Macromer 35KDLA: To a mixture of 15 g PEG, 0.84 g Dioxanone and 0.01 g catalyst was also added 0.39 g d,l-lactide. The mixture was dried, then incubated at 185° overnight; dissolved in chloroform and precipitated in ether, filtered and vacuum-dried; and acrylated with excess acryloyl chloride and triethylamine.

We claim:

1. A biodegradable, polymerizable macromer having a solubility of at least one gram/liter in an aqueous solution at a temperature in the range between about 0 and 50° C. comprising at least one water-soluble region, at least one biodegradable region, and at least one reactive polymerizable group or region capable of crosslinking with other macromers, wherein the polymerizable regions are separated from each other by at least one biodegradable region, and wherein at least one biodegradable region comprises a carbonate or dioxanone linkage.

2. The macromer of claim 1 wherein the water soluble region is attached to a biodegradable region and at least one polymerizable group or region is attached to the biodegradable region.

3. The macromer of claim 1 wherein the water soluble region forms a central core, at least two biodegradable regions are attached to the core, and at least two polymerizable groups or regions are attached to the biodegradable regions.

4. The macromer of claim 1 wherein the biodegradable region is a central core, and at least one polymerizable group or region is attached to said core so that each polymerizable region is separated from each other polymerizable group or region by at least one biodegradable linkage or region.

5. The macromer of claim 1 wherein the water soluble region is a macromer backbone, the biodegradable region is a branch or graft attached to the macromer backbone, and at least two polymerizable groups or regions are attached to the biodegradable regions.

6. The macromer of claim 4 having two or more polymerizable groups or regions attached to the core.

7. The macromer of claim 1 wherein the water soluble region is a star backbone, the biodegradable region is a branch or graft attached to the water soluble star backbone, and at least two polymerizable groups or regions are attached to one or more biodegradable branch or graft, so that each polymerizable group or region is separated from each other polymerizable group or region by at least one biodegradable linkage or region.

8. The macromer of claim 1 wherein the biodegradable region is a star backbone, the water soluble region is a branch or graft attached to the biodegradable star backbone, and two or more polymerizable groups or regions are attached to the biodegradable backbone so that each polymerizable group or region is separated from each other polymerizable group or region by at least one biodegradable linkage or region.

9. The macromer of claim 1 wherein the water soluble region is also the biodegradable region.

10. The macromer of claim 1 wherein the water soluble region is also the biodegradable region, and one or more additional biodegradable regions are grafts or branches upon the water soluble region.

11. The macromer of claim 1 comprising a water-soluble core, at least two biodegradable extensions on the core, and an end cap on at least two extensions, wherein the core comprises poly(ethylene glycol);

at least one of the extensions comprises a biodegradable carbonate or dioxanone linkage; and each end cap comprises a group or region which is polymerizable by a free-radical reaction.

12. The macromer of claim 1 wherein at least one of the extensions comprises a biodegradable poly(hydroxy acid).

13. The macromer of claim 11 wherein the poly(ethylene glycol) has a molecular weight between about 400 and 40,000 Da;

the extensions have a molecular weight between about 200 and 2000 Da; and the polymerizable group or region has a molecular weight between about 50 and 200 Da.

14. The macromer of claim 13 wherein the poly(ethylene glycol) oligomers have a molecular weight of about 20,000 Da; the extensions have a molecular weight about 1000 Da; and the polymerizable groups have a molecular weight of about 50 Da.

15. The macromer of claim 1 wherein the polymerizable groups contain a carbon-carbon double bond capable of cross-linking and polymerizing macromers.

16. The macromer of claim 1 wherein crosslinking and polymerization of the macromer are initiated by a light-sensitive free-radical polymerization initiator with or without a cocatalyst, further comprising a free radical polymerization initiator.

17. The macromer of claim 16 wherein the initiator is selected from the group consisting of xanthine dyes, acridine dyes, thiazine dyes, phenazine dyes, camphorquinone dyes, and acetophenone dyes.

18. The macromer of claim 17 wherein the initiator is selected from the group consisting of eosin, ethyl eosin, 2,2-dimethyl-2-phenyl acetophenone, and 2-methoxy-2-phenyl acetophenone.

19. The macromer of claim 1 wherein crosslinking or polymerizations are initiated in situ by light having a wavelength of 320 nm or longer.

20. The macromer of claim 1 wherein at least one biodegradable region is selected from the group consisting of poly (alpha-hydroxy acids), poly(lactones), poly(amino acids), poly(anhydrides), poly(orthoesters), and poly (phosphoesters).

21. The macromer of claim 20 wherein the poly(alpha-hydroxy acid) is selected from the group consisting of poly(glycolic acid), poly(D,L-lactic acid) and poly(L-lactic acid).

22. The macromer of claim 20 wherein the poly(lactone) is selected from the group consisting of poly(epsilon-caprolactone), poly (delta-valerolactone) and poly(gamma-butyrolactone).

23. The macromer of claim 1 wherein the water soluble region is selected from the group consisting of poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, polysaccharides, carbohydrates, proteins, and combinations thereof.

24. The macromer of claim 1 further comprising a prophylactic, therapeutic or diagnostic agent.

25. The macromer of claim 1 comprising at least two water soluble regions linked to each other by at least one carbonate or dioxanone linkage.

26. The macromer of claim 1 comprising a core of two or more water soluble regions linked by carbonate or dioxanone linkages.

27. The macromer of claim 26 wherein at least two biodegradable groups or regions are attached to the core and at least two polymerizable groups are attached to the biodegradable groups or linkages.

28. The macromer of claim 1 wherein the carbonate linkage is prepared from a cyclic aliphatic carbonate.

29. The macromer of claim 1 wherein the carbonate linkage is prepared from trimethylene carbonate.

30. The macromer of claim 1, wherein two or more polymer blocks are linked by linkages comprising carbonate groups to obtain a higher molecular weight of reactive macromer without compromise of biodegradability.

31. The macromer of claim 30, wherein the average number of polymer blocks in each macromer is two or more.

32. The macromer of claim 1, in which the one or more reactive polymerizable group(s) are selected from ethylenically or acetylenically unsaturated groups, isocyanates, epoxides (oxiranes), sulfhydryls, succinimides, maleimides, amines, imines, amides, carboxylic acids, sulfonic acids and phosphate groups.

33. The macromer of claim 32, in which the one or more reactive polymerizable group(s) are selected from an ethylenically-unsaturated group.

34. The macromer of claim 33, in which the ethylenically-usaturated group is selected from vinyl groups, allyl groups, unsaturated monocarboxylic acids, diacrylates, oligoacrylates, unsaturated dicarboxylic acids, and unsaturated tricarboxylic acids.

35. The macromer of claim 32, in which the reactive polymerizable groups are found on more than one type of macromer.

36. The macromer of claim 35, in which a first macromer comprises a reactive group selected from an amine, an alcohol, and a thiol, and a second macromer comprises a reactive group selected from isocyanate, isothiocyanate, aldehyde, epoxide, oxirane (epoxide), succinimides, maleimides and cyclic imines.

* * * * *